United States Patent [19]
Brown et al.

[11] Patent Number: 5,842,785
[45] Date of Patent: Dec. 1, 1998

[54] ORTHOPEDIC BONE CEMENT MIXING DEVICE WITH SYRINGE DISPENSER

[75] Inventors: Tim Brown, Kidderminster; David Foster, Virginia Water, both of England

[73] Assignee: Summit Medical Ltd., Gloucester, England

[21] Appl. No.: 696,917

[22] PCT Filed: Feb. 22, 1995

[86] PCT No.: PCT/GB95/00365

§ 371 Date: Nov. 7, 1996

§ 102(e) Date: Nov. 7, 1996

[87] PCT Pub. No.: WO95/22402

PCT Pub. Date: Aug. 24, 1995

[30] Foreign Application Priority Data

Feb. 22, 1994 [GB] United Kingdom .................. 9403362

[51] Int. Cl.⁶ .................................................. B01F 13/06
[52] U.S. Cl. .......................................... 366/139; 366/243
[58] Field of Search ................................... 366/130, 139, 366/189, 242–247, 276, 277, 309, 312, 313; 206/219–221

[56] References Cited

U.S. PATENT DOCUMENTS

| | | | |
|---|---|---|---|
| 1,948,431 | 2/1934 | Rolph | 366/243 |
| 3,009,686 | 11/1961 | Kaplan | 366/276 |
| 3,115,664 | 12/1963 | Del Ponte | |
| 3,606,094 | 9/1971 | Mills | |
| 4,758,096 | 7/1988 | Gunnarsson | |
| 4,961,647 | 10/1990 | Coutts et al. | |
| 4,973,168 | 11/1990 | Chan | 366/139 |
| 5,252,301 | 10/1993 | Nilson et al. | 366/139 X |
| 5,265,956 | 11/1993 | Nelson et al. | |
| 5,328,262 | 7/1994 | Lidgren et al. | 366/139 |
| 5,348,391 | 9/1994 | Murray | 366/139 |

FOREIGN PATENT DOCUMENTS

| | | |
|---|---|---|
| 0 178 658 | 4/1986 | European Pat. Off. |
| 883326 | 7/1953 | Germany |
| 912237 | 12/1962 | United Kingdom |
| 1430064 | 3/1976 | United Kingdom |

*Primary Examiner*—Charles E. Cooley
*Attorney, Agent, or Firm*—Alix, Yale & Ristas, LLP

[57] ABSTRACT

A bone cement mixing apparatus comprises a cylindrical syringe body which functions as a mixing chamber, a mixing element rotatably mounted in the mixing chamber and a drive for causing rotation of the mixing element. The drive includes a handle which is axially movable relative to the mixing chamber and a gear mechanism which couples the handle to the mixing element and translates linear handle motion into rotary mixing element motion. The drive is supported by a chamber lid which engages the syringe body and the lid and drive may be detachable from the syringe body and from the mixing element thereby allowing the lid assembly and drive to be reused.

10 Claims, 3 Drawing Sheets

ORTHOPEDIC BONE CEMENT MIXING DEVICE WITH SYRINGE DISPENSER

BACKGROUND OF THE INVENTION

1. Field of the Invention

The present invention relates to a device for mixing and delivering orthopaedic bone cement or the like.

2. Description of the Prior Art

Orthopaedic bone cement is used throughout the world to secure hip, knee and other metallic prostheses in an appropriate anatomical position. The bone cement is produced by thoroughly mixing together two components, usually methylmethacrylate monomer liquid and polymethylmethacrylate powder. The mixing is usually carried out using a simple bowl and spatula. The surgeon then removes the required amount of cement and manipulates it by hand before inserting it into a preformed cavity or applying it to a resected bony surface where the prosthesis is to be positioned. Cement may either be applied by hand or may be put into a syringe and applied thereby. However, this simple mixing method has two major drawbacks.

Firstly, free methylmethacrylate fumes are emitted from the mixture. It is desirable to remove these fumes, or prevent them from escaping into the atmosphere, since they have an unpleasant odour and may be harmful to operating room personnel. The fumes are known to cause nausea and giddiness and are generally objectionable, particularly to the nurses who actually carry out the mixing. Recently there has also been concern that long term exposure to these fumes results in a more serious health risk. Current employment law relating to occupational health dictates that medical staff must now be protected against the exposure to hazardous substances.

Secondly, a very high mixing efficiency is required to produce a homogenous cement material. During the mixing process air is naturally introduced into the mixture since air is inherently existent within the powder and also in and around the mixing vessel. Air bubbles are also produced by the "boiling off" of monomer which occurs during the mixing process. The introduction of air produces a weak cement and, since the joint must usually support a heavy load, it is important to reduce the amount of air in the mixture as much as possible in order to improve the mechanical strength of the cement material.

In order to eliminate as much air as possible from the mixture, mixing is now preferably carried out under vacuum. This considerably reduces the amount of air in the mixture. Mixing in a conventional bowl and spatula system can produce a product with a porosity value of approximately 20 to 25%. In a vacuum mix, the porosity is often reduced to levels below 5%.

Several devices for mixing the cement in a vacuum are presently available. Some of these are in the form of hand-held mixing bowls. The substances to be mixed are placed in the bowl to which a vacuum is applied. The substances are mixed by means of a rotating paddle extending into the bowl which is rotated manually by means of a handle extending through the lid of the bowl. In some applications, the use of such a mixing bowl, an example of which is disclosed in WO 93/10892, is favoured. Many surgeons prefer to "hand pack" the cement. Bowl mixing also tends to be preferred by nurses who are used to the convenience of mixing in such a vessel; a bowl is easy to use and it is important that the nurses feel confident since timing is very crucial and the mixture must be 'right first time'.

Many surgeons also tend to prefer bowl mixers because they can easily take samples of the cement from the bowl at any time to determine the progress of polymerisation as it is crucial that the mixture does not begin to set before it is applied.

However, in some applications it is preferable or necessary to apply the mixed cement to the bone by means of a syringe. Indeed some surgeons, particularly in Europe, prefer syringe-type application to "hand packing". If the cement is mixed in a bowl, it must then be transferred to a dispensing syringe which can be messy and time consuming and may expose the mixture to more air entrapment. This problem has been overcome by combining a mixing chamber with a syringe. For example, EP-A-0178658 discloses a device for mixing bone cement comprising a mixing container connected to a feed device. A vacuum source is connected to the feed device for mixing the substances under vacuum. This device has proved to be a very efficient mixing and transfer system and eliminates the need to transfer the mixed cement from the mixing bowl to a syringe.

However, a device such as disclosed in EP-A-0178658 may be inadequate in that 'dead spots', i.e. areas where the components are not sufficiently mixed, occur, particularly at the outer edges of the mixing chamber.

Further, the mixing paddle of EP-A-0178658 is rotated by a rotary electric drive motor. This makes the device costly and space consuming and requires specialist and time-consuming installation. The device is not easily portable and its use is, therefore, not particularly flexible.

U.S. Pat. No. 4,758,096 also discloses a bone cement mixer in which the cement is mixed in the dispensing vessel. In this device, the mixing is effected manually by means of a "masher" plate-type agitator. The masher plate is attached to a shaft attached to a handle. The agitator is movable in the chamber both axially and rotatably to permit mixing of the cement by the user moving the handle vertically and rotatably. However, such a mixing operation is difficult and inefficient and does not result in thorough mixing of the cement, leaving areas of unmixed powder.

SUMMARY OF THE INVENTION

The present invention aims to overcome the above-mentioned problems.

According to one aspect of the invention, there is provided a bone cement mixing apparatus comprising a mixing chamber, a mixing element rotatably mounted in said mixing chamber, and drive means for causing rotation of said mixing element, wherein said drive means comprises a handle axially movable relative to said mixing chamber, and a gear mechanism between said handle and said mixing element such that said gear mechanism translates axial movement of said handle into rotation of said mixing element.

According to another aspect of the invention, there is provided a method of mixing bone cement in a mixing chamber, by a mixing element rotatably mounted in said chamber containing the material to be mixed; said method comprising axially moving a drive handle, relative to said chamber, wherein said handle is connected to said mixing element via a gear mechanism, such that axial movement of said handle is translated via said gear mechanism into rotation of said mixing element.

The preferred type of gear mechanism for use in the practice of the present invention is a "barley twist" mechanism wherein a downwards stroke of the handle moves a threaded rod axially through a threaded gear housing in the form of a drive bush coupled to the mixing element imposing a rotational force in a first direction on the mixing element. On the upward stroke of the handle, the mixing element is caused to rotate in the opposite direction. Rotating the element alternately in different directions during mixing provides very thorough mixing. The "barley twist" mechanism allows this with a simple push-pull action of the handle rather than the user having to rotate the handle backwards and forwards alternately which can be difficult and tiring, particularly when mixing cement of high viscosity.

Although the present invention may be applied to any bone cement mixing chamber, it is preferably used in combination with a dispensing syringe. Thus, the cylinder of the syringe forms the body of the mixing chamber and a plunger is slidably mounted at one end of the cylinder for causing ejection of the mixed cement.

As discussed above, the quality of the cement is greatly improved if it is mixed under vacuum and, therefore, in a preferred embodiment, the invention comprises means for creating a vacuum within the chamber.

For thorough mixing, the mixing element is preferably in the form of a paddle arrangement mounted on a shaft which in the preferred embodiment includes an axial bore through which the threaded rod of the barley twist gear mechanism can extend. The paddle or paddles extend radially from the shaft and at least one paddle may extend from the shaft to the wall of the mixing chamber so that as it rotates it wipes out the whole of the cement containing part of the interior of the chamber.

To avoid wasting any of the mixed cement, the mixing paddle should preferably be wiped clean before it is removed from the mixing chamber. A hygienic way of doing this, which avoids contamination of the cement is to provide a slot in the chamber through which the mixing paddle extends into the chamber. This slot is of a width substantially equal to the thickness of the mixing paddle so as to wipe any residual cement from the mixing paddle as it is withdrawn through the slot after mixing.

The slot may be formed as an integral part of the cylinder towards the end to which the handle is attached, in which case, after mixing, the cement would be ejected through this slot. Alternatively, the slot could be formed in a separate member, such as a cap or a plate, adapted to be inserted between the cylinder and the lid. The slotted member could then be removed after the mixing paddle has been withdrawn through it, before the cement is ejected.

In mixing bone cement, alternate layers of cement powder and monomer liquid are put into the mixing chamber. Initially the cement is very stiff and a high force is needed to start the mixing. There is then a surface reaction between the powder and liquid phases and once mixing has started the required mixing force drops sharply. The larger the interface area between the layers, the better the surface reaction. Thus, the cylinder should be as wide as possible to maximise the layer interface area whilst still being comfortable to handle.

In one embodiment, the mixing element, the handle and the gear mechanism are formed as an integral unit in a detachable lid assembly. The lid is adapted to be attached to one end of the cylinder by e.g. matching threaded portions. After mixing, the lid assembly including the mixing assembly comprising the mixing element, the handle and the gear mechanism can be removed from the cylinder, e.g. by unscrewing, and, in the preferred embodiment, can be replaced by a nozzle or the like. The nozzle cooperates with the plunger to eject the mixed cement out through the nozzle when the plunger is pushed into the cylinder. The plunger may be manually operated, e.g. using a hand gun arrangement or, alternatively, a gas powered pressure gun could be used.

In many applications, however, e.g. in hip replacement operations, more than one step is involved and, therefore, several batches of cement need to be mixed. To make the system more economical, the handle and the gear mechanism should preferably be re-usable, whereas the mixing paddle is only used once and then disposed of. Thus, for such applications the drive mechanism should be detachable from the mixing element after use.

According to a third aspect of the invention, there is provided a bone cement mixing apparatus comprising a mixing chamber, a mixing element rotatably mounted in said mixing chamber, and drive means including a handle for causing rotation of said mixing element, wherein said drive means is carried by a lid assembly of the chamber, and wherein the lid assembly and drive means are detachable from the chamber and from the mixing element thereby enabling reuse of the lid assembly and drive means with a different chamber and mixing element if desired.

Air tight seals are preferably provided between the lid assembly and the mixing element, between the lid assembly and the chamber and the chamber and the stand assembly. In this embodiment the drive bush of the preferred gear mechanism is preferably detachable from the paddle and may conveniently be push fitted into the top of the paddle shaft. A rib and groove locating arrangement is preferred.

When the contents of the chamber have been sufficiently mixed, the lid assembly and drive means can be removed, leaving the paddle inside the chamber. This indicates to the nurse that the next step is to remove the paddle and attach a nozzle for applying the cement. If the paddle is withdrawn through a slit to wipe it clean, it is easier to align the paddle with the slit once the lid assembly has been removed. This makes the device particularly user friendly.

The nozzle cooperates with the plunger to eject the mixed cement out through the nozzle when the plunger is pushed into the cylinder. The plunger may be manually operated, e.g. using a hand gun arrangement or, alternatively, a gas powered pressure gun could be used.

According to another aspect, the invention provides an orthopaedic bone cement mixing apparatus comprising a cylindrical syringe body defining a mixing chamber, a plunger slidably mounted at one end of the cylinder, a mixing member rotatably mounted in said chamber and drive means for causing rotation of said mixing member, wherein said mixing member includes a blade mounted on and radially extending from a rotatable shaft along the central axis of the cylinder such that rotation of said shaft causes said blade to rotate about the axis of the shaft within the interior of the cylinder, and wherein the blade extends from the shaft to the inner wall of the cylinder and is adapted and arranged so that as the blade rotates it wipes out the whole cement containing part of the interior of the cylinder.

BRIEF DESCRIPTION OF THE DRAWING

Preferred embodiments of the invention will now be described, by way of example only, with reference to the accompanying drawings, wherein:

FIG. 4 is a cross-sectional view of a mixing device according to one aspect of the invention, with a nozzle attached and in a cement dispensing position; and FIG. 5 is a top view, on an enlarged scale, of a cover of a syringe body in accordance with the invention.

Referring to FIG. 1, there is shown a combined bone cement mixing and dispensing syringe. The cylindrical syringe body 1 defines a mixing chamber 2. A plunger 3 for ejecting the mixed cement is slidingly located in one end of the cylinder 1. A mixing element extends into the mixing chamber 2. The mixing element comprises a hollow shaft 4 along the central axis of the cylinder 1 with a number of fixed paddle blades 5 extending radially outwards from the shaft 4. The blades 5 are made of plastic strong enough to resist bending when mixing viscous cement. However, in order to prevent 'dead spots' occurring and to ensure thorough mixing, diametrically opposite blades should have generally complementary shapes as shown. The shaft 4 is attached to a drive mechanism including a handle 7 and a gear mechanism which is indicated generally at 6 (shown in more detail in FIG. 2 and discussed further, below). The handle 7 carries a rod 8 which is axially movable by the handle 7. The rod 8 extends axially through the removable lid 9 of the cylinder 1 and passes through a drive bush 10 fixed to the mixing paddle shaft 4 and shown in more detail in FIG. 2. The handle 7 is preferably secured tightly to the rod 8 such that axial motion of the handle 7 necessarily results in rotation of the rod and hence the paddle shaft 4. The rod 8 of the preferred embodiment has a barley twist configuration of square cross-section. The rod 8 passes through the drive bush 10 via a correspondingly dimensioned square aperture 11 which functions as a driving lug. As the drive handle 7 is pushed, the rod 8 moves axially through aperture 11 and into the hollow shaft 4 of the mixing member. Thus, as the rod 8 moves axially through the aperture 11, the square shape of the aperture is forced to follow the 'twist' of the rod 8, thus causing the bush 10, and mixing paddle to rotate as the handle 7 and hence the rod 8 are moved axially. Similarly, when the handle 7 is pulled the rod 8 is withdrawn through the aperture 11 in the bush 10 and the mixing member is caused to rotate in the opposite direction. Thus, as the handle is pushed and/or pulled the mixing blades 5 rotate within the mixing chamber about the axis of the shaft 4.

Figure 1:
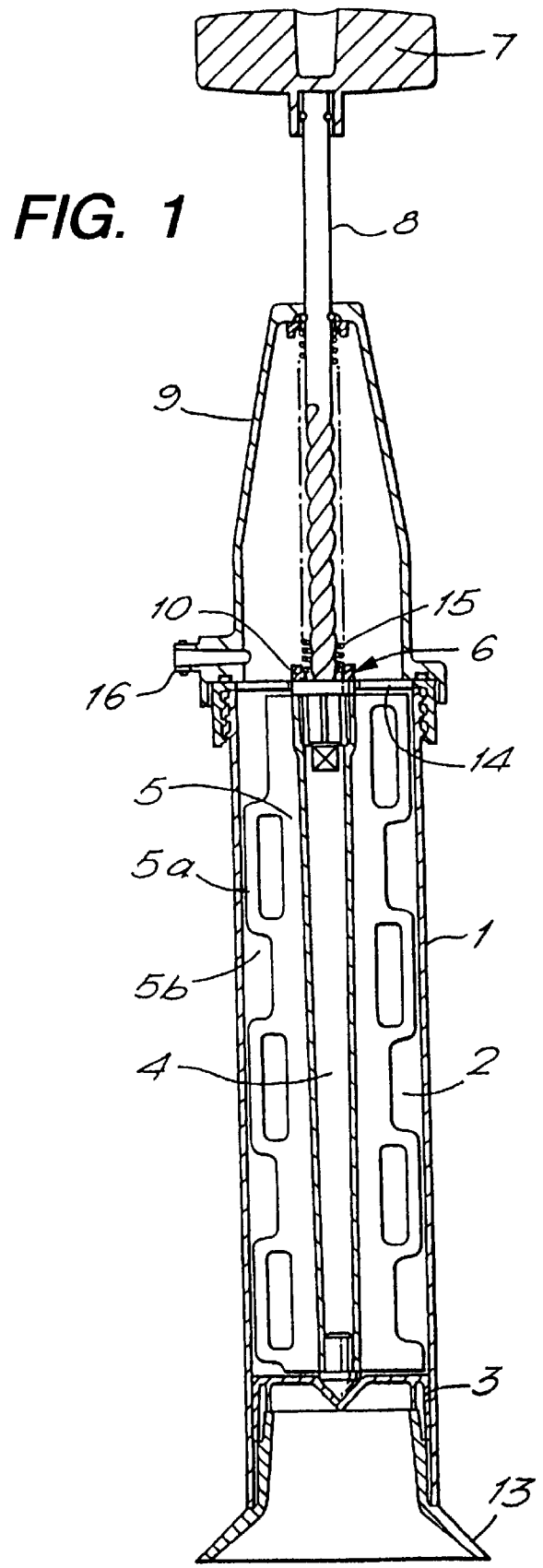
FIG. 1 is a cross-sectional view of a mixing apparatus according to the present invention.
Figure 2:
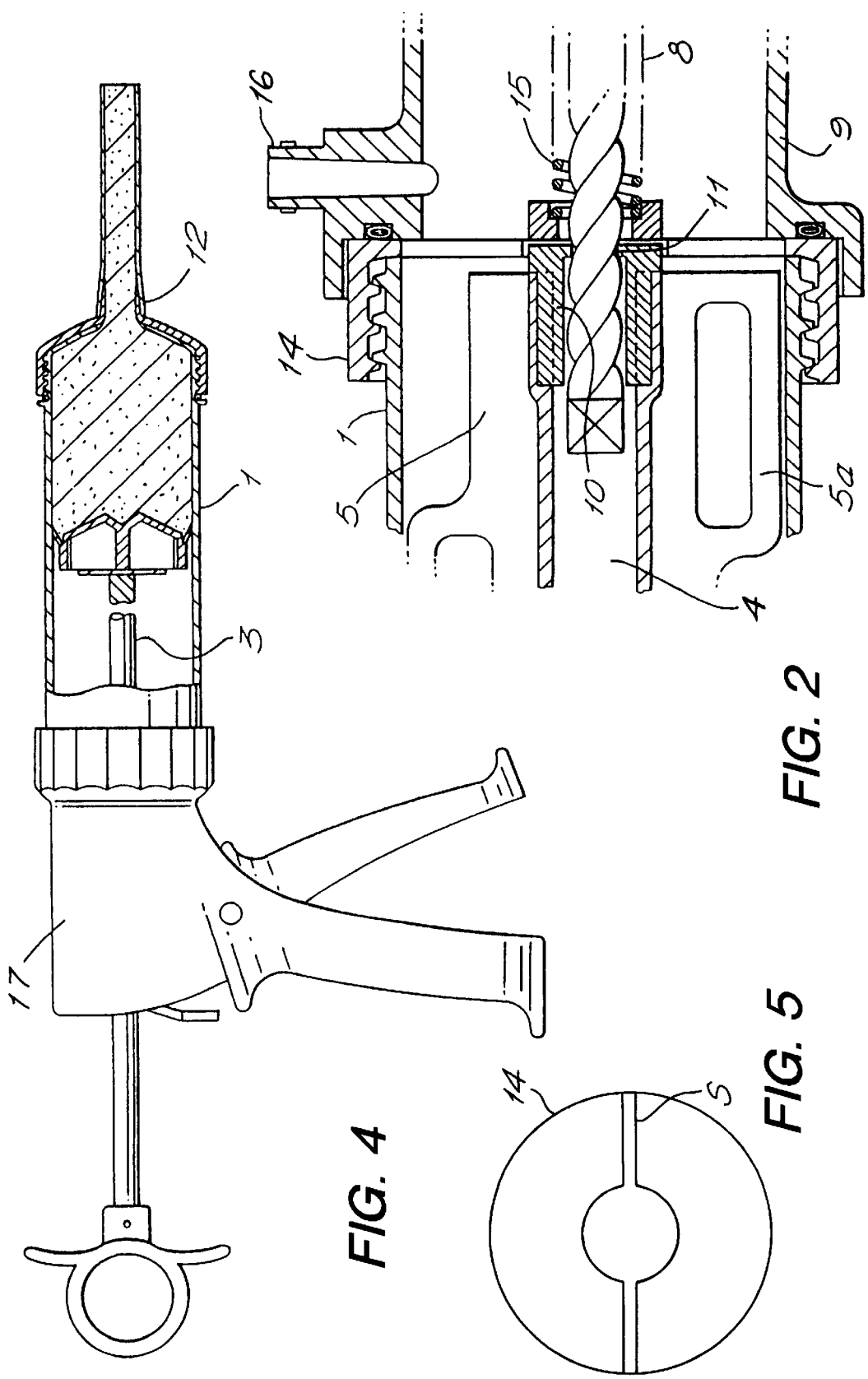
FIG. 2 is a more detailed cross-sectional view of the gear mechanism of a mixing apparatus according to one aspect of the invention.

The drive bush 10 is rotatably mounted inside the lid 9 and, in the embodiment of FIG. 1, the shaft 4 of the mixing member is fixedly attached to the drive bush 10.

Figures 3, 3A:
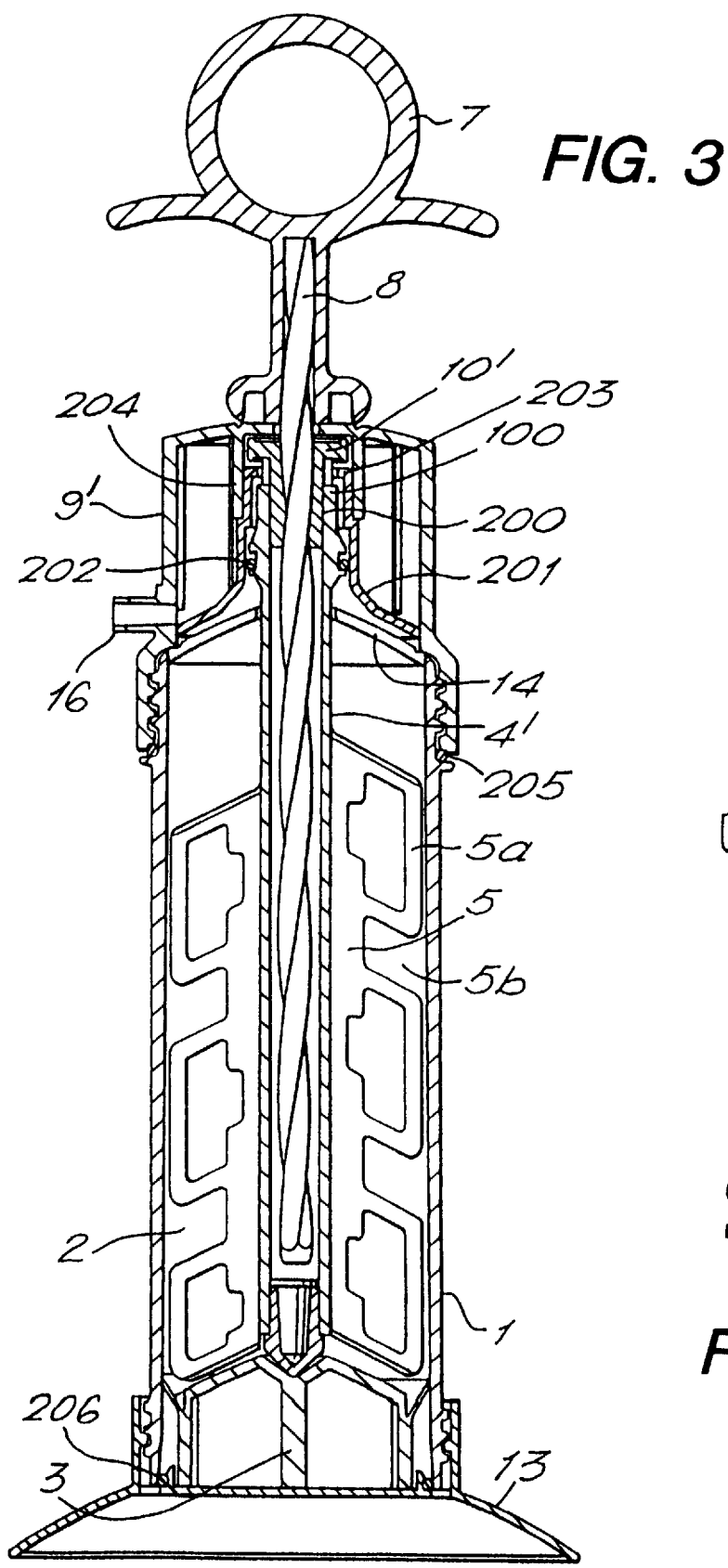
FIG. 3 is a cross-sectional view of a mixing apparatus according to another aspect of the invention.
FIG. 3a, is an enlarged exploded view of the engagement between the mixing paddle and gear mechanism of FIG. 3.

In the embodiment of FIG. 3, the mixing element is instead detachable from the lid assembly. Thus, the drive bush 10' has a number of locating ribs 100 around its outer periphery (FIG. 3A). The mixing member has a hollow shaft 4'. The top of the shaft 4' of the mixing member has a number of grooves 200, corresponding to the ribs 100, around its inner periphery. Towards the open end of the shaft 4', the grooves 200 open out to provide a widened entrance for the ribs 100. This enables easy push-fit location of the drive bush 101 in the shaft 4'. As in the first embodiment, the drive bush has an aperture shaped to cooperate with the rod 8 and translate axial movement of the rod into rotation of the mixing element. As shown in FIG. 3, the lid 9' carries a downwardly facing funnel shape guide member 201 which helps locate the top of shaft 4' to facilitate its engagement by the drive bush 10'. An O-ring seal 202 fitted into a groove on the exterior of shaft 4' cooperates between the top of shaft 4' and the inner surface of the neck of guide member 201 so as to prevent air entering the mixing chamber via the drive gear mechanism.

The top end 203 of guide member 201 is fixed into a downwardly projecting annular flange 204 of the lid 9' so as to retain the rotatable drive bush 10' within the lid assembly.

A further O-ring seal 205 is disposed between the lid 9 and the exterior of cylinder 1.

In the preferred embodiments, the mixing element has two diametrically opposite mixing blades 5 extending radially outwards from the shaft 4. Each blade 5 comprises alternate lobes 5a and spaces 5b along the length of the shaft 4. To ensure thorough mixing, the lobes 5a of one blade 5 correspond to the position of the spaces 5b of the other. Also, the lobes 5a themselves may be solid or apertured as shown. Apertured lobes minimize the amount of material required to form blades which provide sufficiently thorough mixing. Of course any number of blades 5 may be provided and the design of the blades may vary. For example, several blades of different widths could be used.

The mixing chamber 2 is defined by a cylindrical syringe body 1, partially closed at one end. The closed end is adapted to axially receive a plunger 3, This end is also adapted to be received in stand 13 and may be secured to the stand 13 by corresponding screw threads. A seal 206 (FIG. 3) provides a seal between the syringe body 1 and stand 13. The other end of body 1 is preferably provided with an outer thread, adapted to receive a corresponding inner thread of the lid 9 and of a nozzle 12 (FIG. 4).

In use, the cement materials to be mixed are placed into the mixing chamber 2, which is closed at one end by the plunger 3 or part of a plunger. The inner surface of the plunger 3 is preferably domed, as best seen from FIG. 4, to match the inner profile of the lid to minimize waste. The cylindrical body 1 may, after being filled to the desired level, be positioned on the stand 13 or may be hand-held. The lid 9 has an inner thread so that it can be screwed onto the thread at the end of the cylindrical syringe body 1 with the shaft 4 and blades 5 extending into the cylinder 1. The cement is then thoroughly mixed by alternately pushing and pulling the handle 7 which causes the blades 5 to rotate about the axis of the shaft 4. Mixing may be carried out under vacuum and a vacuum pump may be attached to a vacuum port 16 in the lid 9.

When the cement has been mixed sufficiently, the mixing member is removed. In the preferred embodiments, a slotted cover 14 (see also FIG. 5) is provided between the cylinder 1 and the lid 9. Cover 14 has a control aperture, through which the shaft 4 passes, and a slots. In the embodiment of FIG. 3, the paddle is initially left behind in the cylinder 1 after the rod 8 has been withdrawn. The drive bush 10' detaches from the top of the shaft 4' and may be removed when the lid assembly 9 is unscrewed. The paddle can then be withdrawn separately through the slot S in cover 14, the slot being of substantially the same width as the thickness of the blades 5 so that any cement remaining on the blades 5 is wiped off. In the embodiment of FIG. 1 the paddle is always removed with the handle and lid assembly.

The lid 9 is then replaced by an applicator nozzle 12. The mixed cement is then forced through the nozzle 12 under the action of the plunger 3 to be applied to the appropriate site. Different types of plunger may be used to force the cement out through the nozzle 12 for example, a hand operated gun 17 may be used. However, the preferred embodiment uses a gas powered pressure gun. FIG. 4 shows the apparatus with a hand operated gun for imparting motion to plunger 3 and with a nozzle 12 attached in a dispensing position.

The side of the plunger 3 pushing against the cement is preferably domed to profile the ejection end of the chamber 1 to minimize wastage of cement.

The plunger 3 may be slidably inserted at either end of the cylinder 1 although the preferred embodiment is as described above.

The embodiment of FIG. 1 includes a spring 15 which is compressed on the down stroke of the handle and assists the reverse stroke. This is omitted in the second embodiment.

It is preferable to manufacture the cylinder, mixing mechanism and plunger from a fairly rigid plastic material, thus reducing the cost of the apparatus and providing a disposable mixer. The apparatus could, of course, be made from other materials e.g. lightweight metal.

We claim:

1. A bone cement mixing apparatus comprising:

a syringe body, said syringe body defining a generally cylindrical mixing chamber, said mixing chamber having a central axis and first and second oppositely disposed ends, the first of said ends comprising an end wall having an opening therein, said end wall further comprising a slot extending from said opening;

a plunger mounted within said mixing chamber so as to be initially disposed adjacent said second end thereof, said plunger being slideably movable along said central axis toward said first end of said mixing chamber;

a mixing member rotatably mounted in said mixing chamber, said mixing member including:

a rotatable shaft, said rotatable shaft extending through said opening in said end wall and along said central axis; and at least a first blade mounted on and radially extending from said rotatable shaft, rotation of said shaft causing said blade to rotate about said central axis within the interior of said mixing chamber, said blade having a width and thickness which is generally complementary to the length and width of said slot whereby said blade may pass through said end wall slot, residual cement being scraped off said blade by withdrawal thereof through said slot; and drive means for causing rotation of said mixing member, said drive means including:

a handle located to the exterior of said syringe body at said first end of said mixing chamber, said handle being axially movable relative to said mixing chamber, the movement of said handle being parallel to and in-line with said central axis; and a gear mechanism for connecting said handle to said mixing member, said gear mechanism comprising a barley twist mechanism having a threaded rod, a first end of said rod being connected to said handle, said gear mechanism further having a rotatable drive bush, said drive bush being coupled to said mixing member rotatable shaft for rotation therewith, said drive bush being engaged by said threaded rod whereby axial motion of said handle will cause rotation of said drive bush thereby imparting rotational force to said mixing member.

2. The apparatus of claim 1 wherein said first blade of said mixing member extends from said rotatable shaft to the inner wall of said mixing chamber, said blade being sized and shaped to wipe said inner wall of said chamber during rotation.

3. The apparatus of claim 2 further comprising:

means for creating a sub-atmospheric pressure in said mixing chamber.

4. The apparatus of claim 1 further comprising:

means for creating a sub-atmospheric pressure in said mixing chamber.

5. The apparatus of claim 4 further comprising:

a lid assembly, said lid assembly being removably coupled to said syringe body, said lid assembly supporting said drive means, said end wall being disposed within said lid assembly.

6. The apparatus of claim 5 further comprising:

means for establishing air tight seals between said lid assembly and said mixing member and between said lid assembly and said syringe body.

7. The apparatus of claim 6 further comprising:

a bone cement dispensing nozzle, said nozzle being engageable with said syringe body so as to communicate with said first of said mixing chamber upon removal of said lid assembly.

8. The apparatus of claim 7 wherein said first blade of said mixing member extends from said rotatable shaft to the inner wall of said mixing chamber, said blade being sized and shaped to wipe said inner wall of said chamber during rotation.

9. The apparatus of claim 8 wherein said drive bush is detachably engageable with said mixing member rotatable shaft, engagement and disengagement of said drive bush with said rotatable shaft being accomplished by imparting axial motion to said drive bush.

10. The apparatus of claim 9 wherein a first of said drive bush and rotatable shaft is provided with radially extending ribs and the other of said drive bush and rotatable shaft is provided with grooves which are generally complementary to said ribs whereby said detachable engagement may be accomplished by inserting said ribs into said grooves.

* * * * *